(12) United States Patent  (10) Patent No.: US 7,812,938 B2
Guo et al.                  (45) Date of Patent:     Oct. 12, 2010

(54) INTEGRATED CHEMICAL SEPARATION LIGHT SCATTERING DEVICE

(75) Inventors: Xun Guo, Sacramento, CA (US); Hong Wang, Cupertino, CA (US)

(73) Assignee: Opto Trace Technologies, Inc., Mountain View, CA (US)

( * ) Notice: Subject to any disclaimer, the term of this patent is extended or adjusted under 35 U.S.C. 154(b) by 688 days.

(21) Appl. No.: 11/761,453

(22) Filed: Jun. 12, 2007

(65) Prior Publication Data
US 2008/0309918 A1    Dec. 18, 2008

(51) Int. Cl.
*G01N 21/00* (2006.01)
(52) U.S. Cl. ........................................ 356/72
(58) Field of Classification Search ............. 356/72–73, 356/300, 301
See application file for complete search history.

(56) References Cited

U.S. PATENT DOCUMENTS

| | | | |
|---|---|---|---|
| 4,752,391 A | 6/1988 | Porsch | |
| 4,952,514 A | 8/1990 | Haddad | |
| 5,904,749 A | 5/1999 | Chen | |
| 6,747,735 B2 | 6/2004 | Chen | |
| 6,928,858 B2 | 8/2005 | Lin | |
| 7,195,461 B2 | 3/2007 | Allington | |
| 7,608,818 B2 * | 10/2009 | Miller et al. | 250/288 |

* cited by examiner

*Primary Examiner*—Tarifur Chowdhury
*Assistant Examiner*—Abdullahi Nur
(74) *Attorney, Agent, or Firm*—Xin Wen

(57) ABSTRACT

An integrated chemical separation device includes a single device body, a chemical separation unit configured to separate a chemical from a fluid, a Raman sensor substrate comprising one or more surfaces configured to be adsorbed by molecules of the chemical from the fluid, and a Raman scattering spectrometer unit that can emit a laser beam to illuminate the Raman sensor substrate and to detect the chemical from the light scattered from the Raman sensor substrate. The chemical separation unit, the Raman sensor substrate, and the Raman scattering spectrometer unit are held in or mounted to the single device body.

43 Claims, 4 Drawing Sheets

INTEGRATED CHEMICAL SEPARATION LIGHT SCATTERING DEVICE

RELATED APPLICATIONS

The present patent application is related to commonly assigned pending U.S. patent application Ser. No. 10/852,787, entitled "Method of fabricating nano-structured surface and configuration of surface enhanced light scattering probe", filed May 24, 2004, and U.S. patent application Ser. No, 11/562,409, entitled "Arrays of nano structures for surface enhanced Raman scattering", filed Nov. 21, 2006. U.S. patent application Ser. No. 10/852,787 claims priority to provisional U.S. patent applications 60/473,283 and 60/473,287, both filed on May 27, 2003, and provisional application 60/520,222 filed on Nov. 17, 2003. U.S. patent application Ser. No. 11/562,409 claims priority to provisional U.S. patent application 60/751,472, filed Dec. 19, 2005. The content of the above patent applications are incorporated herein by reference.

BACKGROUND

The present application relates to chemical separation methods and apparatuses.

In many fields, such as environmental monitoring and protection, airport security, food safety, and disease detection and diagnosis, it is often necessary to detect and identify the chemical compositions of an unknown sample. This task is often performed by the first isolating the different, compounds in the sample, and then applying an identification technique to each isolated compound. A standard method for isolating unknown compounds in a gas or liquid phase is called gas chromatography (GC), where the unknown sample is transformed into a carrier gas, if not already in the gaseous state, and the various compounds in the gas are separated due to their differing gaseous properties, such as polarity, affinity to the column and surrounding condition, etc. A standard method for isolating unknown compounds in a liquid phase is called liquid chromatography (LC).

Once the compounds are isolated, they may be identified. The simplest way to identify the compounds is by noting the retention time it takes for each compound to pass through the gas or liquid chromatograph, since different compounds take different amounts of retention time to do so. But this method is limited to samples where much is known about the components and need pure standards to get their retention time at the same running conditions.

A more powerful method for identifying isolated compounds examines the intensity of different wavelengths of light emitted, transmitted, reflected, or scattered by the compound. This technique, called spectroscopy, works if each compound emits, transmits, reflects, or scatters light differently and if the spectroscopic instrument has sufficient spectral resolution to detect these differences. More specifically, different chemical compounds emit, transmit, reflect, or scatter different wavelengths of light with differing intensities. A graph or picture of such data is called the spectrum of that compound. Different types of spectroscopy reproduce the spectrum of a compound over different wavelengths and/or under different conditions. If the type of spectroscopy used provides a unique spectrum for each chemical compound, an unknown compound can be identified by producing its spectrum (for example, by illuminating the compound and measuring the light reflected, scattered, or emitted therefrom) and comparing its spectrum with the spectra of known compounds. As a result, gas or liquid chromatographs, which isolate compounds from a sample, are often used with spectrometers, which identify the compounds once they are isolated.

A challenge for gas or liquid chromatography is to provide a flexible and convenient device while still being able to perform the detection of the sample materials. Another challenge for gas or liquid chromatography is to have high sensitivity in the device such that a minute amount of the trace chemicals can be accurately detected.

SUMMARY

In one aspect, the present invention relates to an integrated chemical separation device includes a single device body, a chemical separation unit configured to separate a chemical from a fluid, a Raman sensor substrate comprising one or more surfaces configured to be adsorbed by molecules of the chemical from the fluid, and a Raman scattering spectrometer unit that can emit a laser beam to illuminate the Raman sensor substrate and to detect the chemical from the light scattered from the Raman sensor substrate, wherein the chemical separation unit, the Raman sensor substrate, and the Raman scattering spectrometer unit are held in or mounted to the single device body.

In another aspect, the present invention relates to an integrated chemical separation device including a single device body; a chemical separation unit configured to separate a chemical in a fluid; a Raman sensor substrate comprising a plurality of rods or holes having diameters in the range from 1 nanometer to 1000 nanometers, wherein the plurality of rods or holes comprise surfaces configured to be adsorbed by molecules of the chemical from the fluid; a fluid conduit configured to transport the fluid to the vicinity of the surfaces to allow the molecules of the chemical to adsorb to the surfaces; and a Raman scattering spectrometer unit that includes a laser source configured to emit the laser beam to illuminate the Raman sensor substrate; and a Raman spectrometer configured to produce a Raman spectrum for detecting the chemical in response to scattered light from the Raman sensor substrate. The chemical separation unit, Raman sensor substrate, and Raman scattering spectrometer unit are held in or mounted to the single device body.

In another aspect, the present invention relates to an integrated chemical separation device that includes a single device body; a chemical separation unit comprising one or more capillary columns configured to separate the chemical from a gas; and an injector configured to inject the gas into the one or more capillary columns; a Raman sensor substrate comprising surfaces configured to be adsorbed by molecules of the chemical from the gas; a fluid conduit configured to transport the gas to the vicinity of the surfaces to allow the molecules of the chemical to adsorb to the surfaces; and a Raman scattering spectrometer unit that includes a laser source configured to emit the laser beam to illuminate the Raman sensor substrate; and a Raman spectrometer configured to produce a Raman spectrum for detecting the chemical in response to scattered light from the Raman sensor substrate. The chemical separation unit, the Raman sensor substrate, and the Raman scattering spectrometer unit are held in or mounted to the single device body.

In yet another aspect, the present invention relates to an integrated chemical separation device that includes a single device body; a separation LC column configured to separate the chemical from a liquid; a first pump configured to pump the liquid through the separation LC column and to the Raman sensor substrate; a Raman sensor substrate comprising surfaces configured to be adsorbed by molecules of the chemical from the liquid; a fluid conduit configured to transport the liquid to the vicinity of the surfaces to allow the molecules of the chemical to adsorb to the surfaces; and a Raman scattering spectrometer unit that includes a laser source configured to emit the laser beam to illuminate the Raman sensor substrate; and a Raman spectrometer configured to produce a Raman spectrum for detecting the chemical in response to scattered light from the Raman sensor substrate. The chemical separation unit, the Raman sensor substrate, and the Raman scattering spectrometer unit are held in or mounted, to the single device body.

Implementations of the system may include one or more of the following. The Raman sensor substrate can include a plurality of rods having diameters in the range from 0.5 nanometers to 1000 nanometers. The Raman sensor substrate can include a plurality of holes having diameters in the range from 0.5 nanometers to 1000 nanometers. The plurality of rods can have heights in the range from 0.5 nanometers to 1000 nanometers. The plurality of holes can have depths in the range from 0.5 nanometers to 1000 nanometers. The Raman sensor substrate can include a plurality of rods or holes having center to center spacing in the range from 0.5 nanometers to 1000 nanometers. The chemical separation unit can separate the chemical from a gas. The chemical separation unit can include one or more capillary columns configured to separate the chemical from the gas. The integrated chemical separation device can further include an injector configured to inject the gas into the one or more capillary columns. The chemical separation unit can separate the chemical from a liquid. The chemical separation unit can include column configured to separate the chemical from the liquid. The integrated chemical separation device can further include a first pump configured to pump the liquid through the chemical separation unit and to the Raman sensor substrate. The integrated chemical separation device can further include a second pump configured to pump an effluent liquid away from the Raman sensor substrate and out of the integrated chemical separation device; and a solvent reservoir configured to provide a solvent to merge with the effluent liquid to be pumped out of the integrated chemical separation device. The integrated chemical separation device can further include one or more valves configured to control a flow of the fluid to one or more surfaces. The Raman sensor substrate can include a fluid conduit configured to transport a liquid to the vicinity of the one or more surfaces to allow the molecules of the chemical to adsorb to the one or more surfaces. The integrated chemical separation device can further include a sensor controller configured to apply a temperature bias, an electric field, or a magnetic field to the Raman sensor substrate to assist adsorption of molecules of the chemical from the fluid on the one or more surfaces. The integrated chemical separation device can further include a chemical separation controller configured to control the chemical separation unit to separate of the chemical from the fluid. The chemical separation controller can control temperature or a pressure of the liquid in the chemical separation unit to assist the separation of the chemical from the fluid. The Raman scattering spectrometer unit can include a laser source that can emit the laser beam to illuminate the Raman sensor substrate; and a Raman spectrometer configured to produce a Raman spectrum in response to scattered light, from the Raman sensor substrate. The integrated chemical separation device can further include a computer processor configured to detect the chemical using the Raman spectrum. The computer processor can be held in or onto the single device body. The integrated chemical separation device can further include a sensor controller configured to control the temperature or to apply an electric field or an magnetic field to the Raman sensor substrate; a chemical separation controller configured to control temperature or pressure of the fluid in the chemical separation unit; and a computer processor configured to control the sensor controller, or the chemical separation controller, or both the sensor controller and the chemical separation controller, wherein the sensor controller, the chemical separation controller, and the computer processor are held in or mounted to the single device body.

Embodiments may include one or more of the following advantages. The disclosed system and methods provide an integrated device that can perform chemical separation and Raman scattering to detect and analyze trace amount of chemicals. The disclosed integrated device can significantly enhance detection sensitivity by using replaceable Raman sensor substrate having nanometer-scale structures and associated surfaces that can adsorb the molecules of the chemical to be detected. The detection sensitivity can also be increased by optimizing the directions of incident laser beam and the scattered laser light relative to the orientations of the nanometer-scale structures in the Raman sensor substrate.

The disclosed system and methods also provide a compact and integrated chemical separation and Raman scattering device with reduced number of components, decreased footprint, and thus reduced system costs. The integrated chemical separation and Raman scattering device can be easily transported and deployed at locations convenient for sample collection, which allows fast measurement turn around. The disclosed systems and methods can also be flexibly applied to a variety of chemical separation technologies such as high performance liquid chromatography (HPLC), gas chromatography (GC), and ion chromatography (IC), etc.

Details of one or more embodiments are set forth in the accompanying drawing and in the description below. Other features, objects, and advantages of the invention will become apparent from the description and drawings, and from the claims.

DETAILED DESCRIPTION

Figure 1:
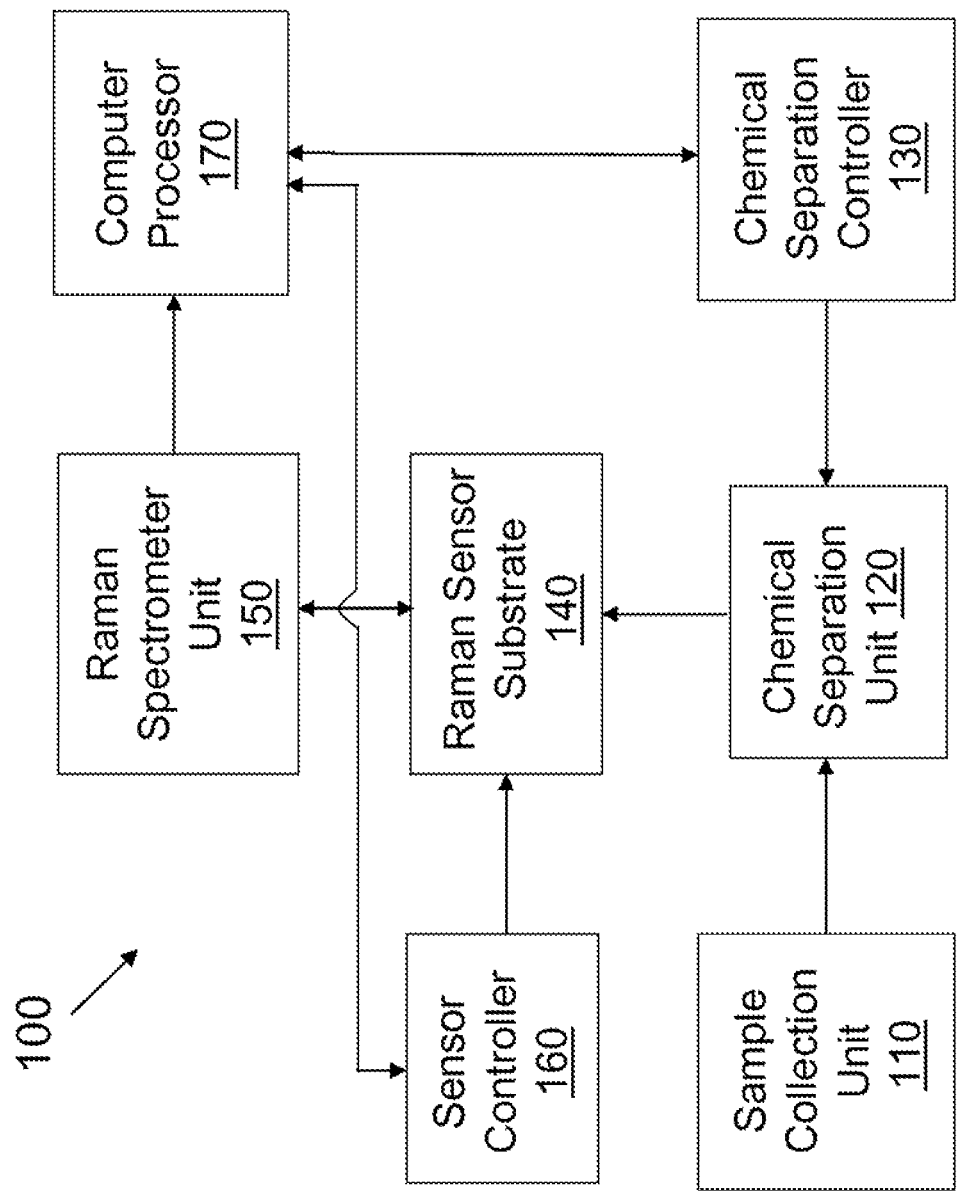
FIG. 1 is a system block diagram of an integrated Raman scattering chemical separation device.

An integrated Raman scattering chemical separation device 100, referring to FIG. 1, can include a sample collection unit 110, a chemical separation unit 120, a chemical separation controller 130, a Raman sensor substrate 140, a Raman spectrometer unit 150, and a sensor controller 160, which can be contained in or held by a single device body as shown in the examples described below. The device body can include a rigid chassis, a chamber, a rigid fixture or frame that can define an enclosure. The sample collection unit 110 can collect samples from gas, liquid, or solid phases. The sample may contain trace chemical that is to be detected and identified by the integrated Raman scattering chemical separation device 100. The chemical separation unit 120 can separate the one or more chemicals contained in the sample under the control of the chemical separation controller 130. As describe in more detail below, the chemical separation controller 130 can control the pressure and the temperature of the fluid in the chemical separation unit 120 to produce more distinct separation of the chemicals. A chemical separated by the chemical separation unit 120 is received by the Raman sensor substrate 140.

Figure 4:
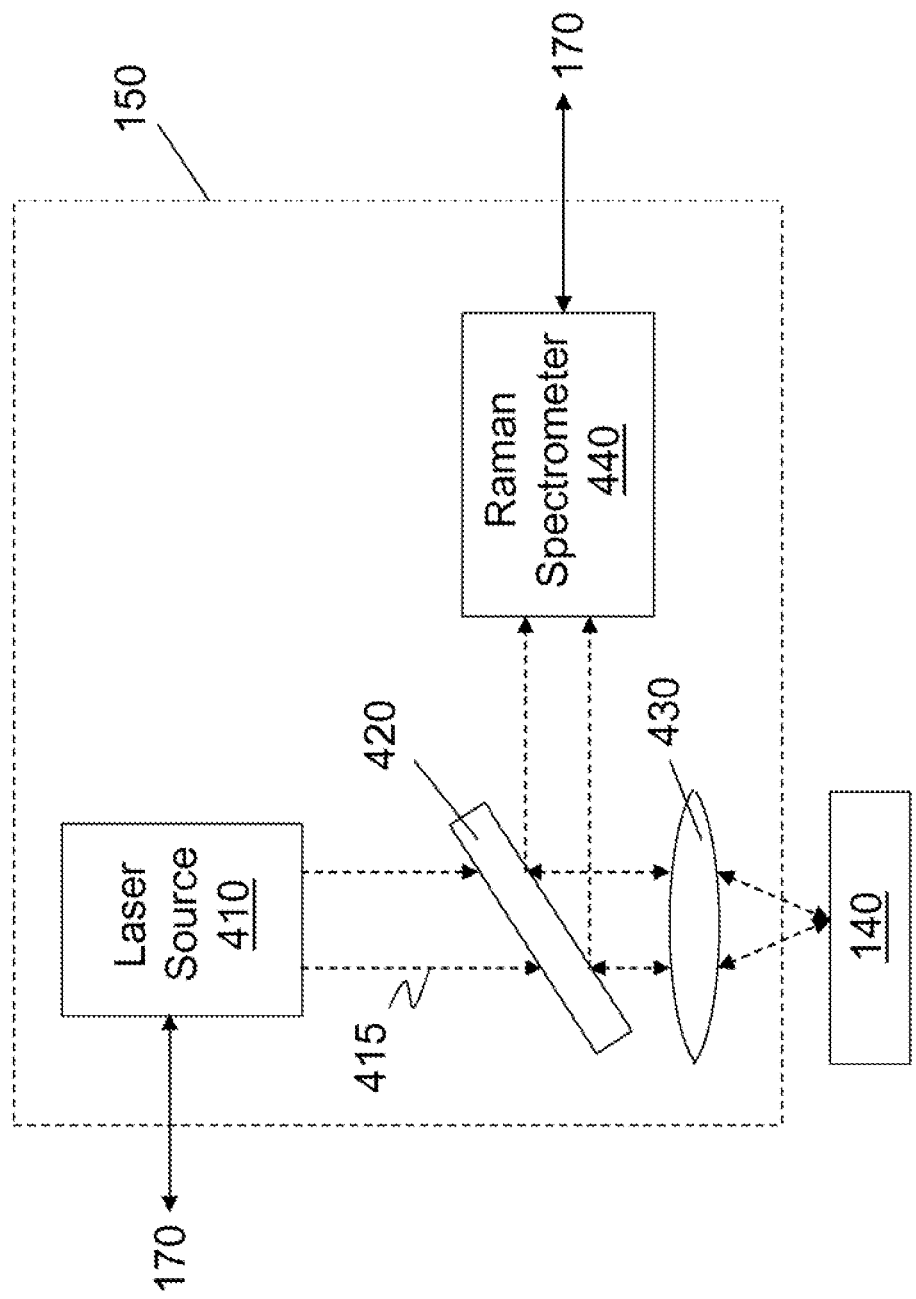
FIG. 4 is a schematic diagram, of an exemplified integrated Raman spectrometer unit compatible with the exemplified integrated Raman scattering gas chemical separation device of FIG. 2 and the exemplified integrated Raman scattering liquid chemical separation device of FIG. 3.

The Raman sensor substrate 140 can include microscopic structures such as an array of rods on a substrate or an array of holes in a substrate. The diameters of the rods or the holes can be in the range from 0.5 to 1000 nanometers. The chemical received by the Raman sensor substrate 140 can be adsorbed by the surfaces of the microscopic structures. As shown in FIG. 4, the Raman spectrometer unit 150 can include a laser source 410 that can emit a laser beam 415. The laser beam 415 can pass a beam splitter 420 and an optical system 430 to illuminate the Raman sensor substrate 140. Light scattered from the Raman sensor substrate 140 can be collected by the optical system 430 and directed to a Raman spectrometer 440 by the beam splitter 420. A Raman spectrum of the chemical adsorbed on the surfaces of the microscopic structures on the Raman sensor substrate 140 can be obtained by the Raman spectrometer 440. The Raman spectrometer 440 and the laser source 410 can be controlled by the computer processor 170.

Referring back to FIG. 1, the Raman spectrum can be analyzed by a computer processor 170, wherein the chemical can be determined by identifying one or more signatures of the chemical in the Raman spectrum. The computer processor 170 can also be held in the same device body. The chemical separation controller and the sensor controller 160 can be controlled by the computer processor 170. The laser source 410 can also be controlled by the computer processor 170. The Raman spectrometer 440 can be controlled by the computer processor 170 and send measured Raman spectral data to the computer processor 170 for analyses and the determination of the chemical.

The surface of the micro structure structures can include a conductive material, which can enhance the signal strength of the Raman spectroscopy. The strength of the Raman scattering signal can be further enhanced by controlling the temperature of the substrate, or apply an electric field or a magnetic field to the substrate by a sensor controller 160. The Raman sensor substrate can include a plurality of holes having diameters in the range from 0.5 to 1000 nanometers. The Raman sensor substrate can include a plurality of rods or holes having center to center spacing in the range from 0.5 to 1000 nanometers, and height or depth of rods or holes in the range from 0.5 nanometers to 1000 nanometers. Details about the structures and the operations of the Raman sensor substrate 140 and the sensor controller 160 are disclosed in the above referenced and commonly assigned U.S. patent application Ser. No. 10/852,787, entitled "Method of fabricating nano-structured surface and configuration of surface-enhanced light scattering probe", filed May 24, 2004, and U.S. patent application Ser. No. 11/562,409, entitled "Arrays of nano structures for surface-enhanced Raman scattering", filed Nov. 21, 2006, the content of which is incorporated herein by reference.

Figure 2:
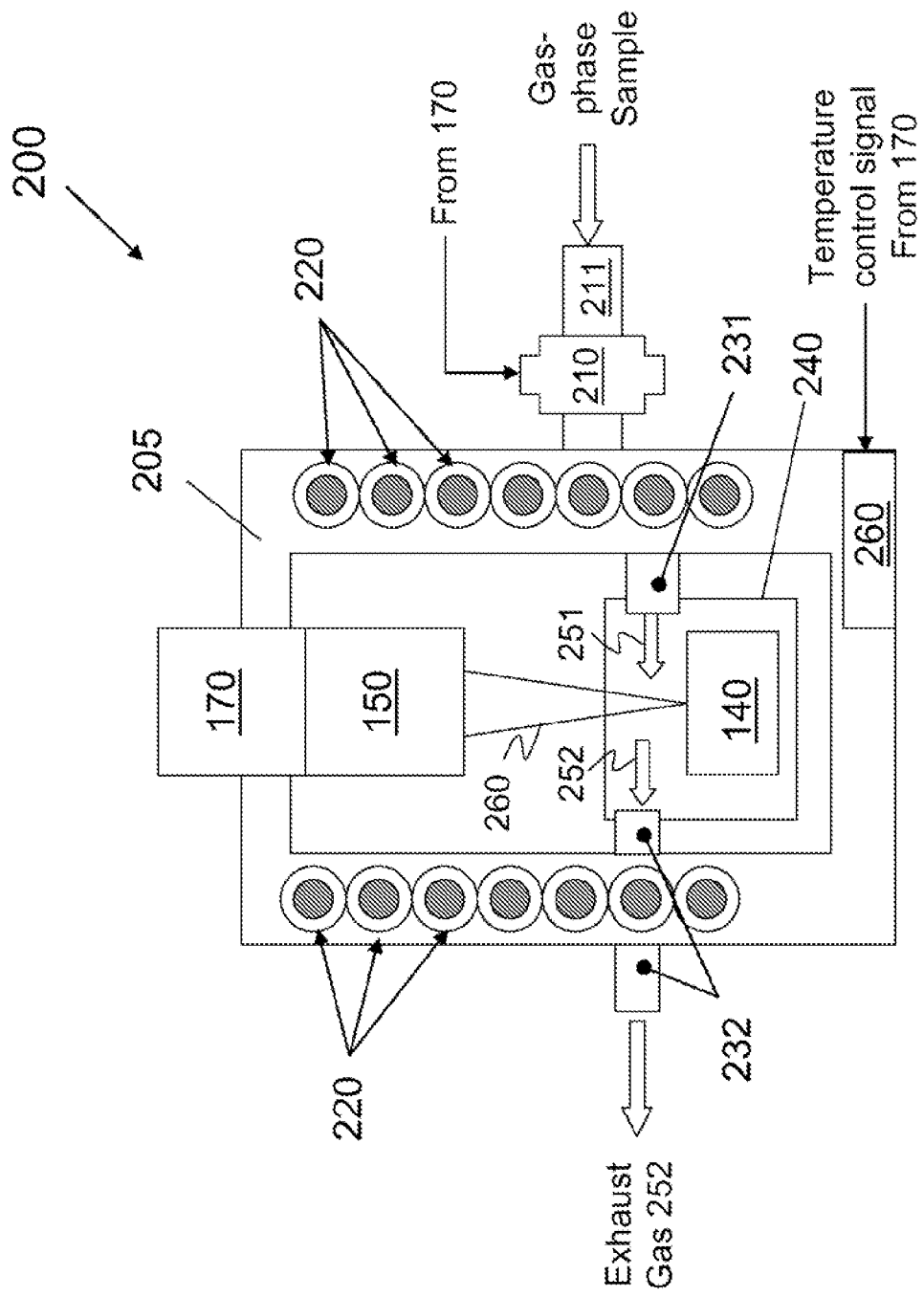
FIG. 2 is a schematic diagram of an exemplified integrated Raman scattering gas chemical separation device.

In an exemplified implementation, referring to FIG. 2, an integrated Raman scattering gas chemical separation device 200 can include a device body 205, an injector 210 and an inlet 211 mounted on the device body 205, one or more capillary columns 220 in fluid connection with the injector 210, a gas chamber 240, and an inlet 251 and an outlet 252 connecting the gas chamber 240 and the exterior of the device body 205. The device body 205 can be a rigid chassis, a rigid frame, or a rigid cylinder that can hold the capillary columns 220, the gas chamber 240, the injector 210 and the inlet 211, and the inlet 251 and the outlet 252. The device body 205 can be formed of metal, glass, or other rigid materials, or a combination of different types of rigid materials. The capillary columns 220 can be made of stainless steel, Teflon, a plastic material, and silicon glass. Different materials can be selected depending on the chemical to be detected. The ends of the capillary columns 220 can be screw-in mountable to the inlet 231 and the injector 210. The injector 210 can inject the gas into the capillary columns 220 and provide pressure difference to push the gas flowing through the capillary columns 220.

A Raman sensor substrate 140 can be held inside the gas chamber. The gas chamber 240 can be made of stainless steel that can enclose the gas samples to a desirable concentration to allow the chemicals to be adsorbed on the microscopic surfaces of the Raman sensor substrate 140. The gas chamber 240 can include a window that allows optical communications between a Raman spectrometer unit 150 and the Raman sensor substrate 140. The Raman spectrometer unit 150 can be held inside or on the device body 205. The integrated Raman scattering gas chemical separation device 200 can further include a temperature controller 260 that is in thermal communication with the capillary columns 220. A computer processor 170 can also be included in the integrated Raman scattering gas chemical separation device 200. The computer processor 170 can also be held inside or on the device body 205. The computer processor 170 can generate the temperature control signal and analyze the Raman spectral signals output from the Raman spectrometer 440 in the Raman spectrometer unit 150. The integrated Raman scattering gas chemical separation device 200 can be built in compact dimensions compared to a collection of conventional gas chemical separation systems and Raman scattering spectroscopy systems. For example, the disclosed integrated Raman scattering gas chemical separation device 200 can have a compact footprint of approximately 100 cm by 10 cm, and a height of 100 cm. In another example, the device body 205 of the integrated Raman scattering gas chemical separation device can have dimensions of 4"×6"×4" (Width×Length×Height).

Because of its compact dimensions, the integrated Raman scattering gas chemical separation device 200 can be easily transported and placed at a location that is easy for gas sample collection. For example, the integrated Raman scattering gas chemical separation device 200 can be placed next to a security check point at an airport or seaport for detecting harmful materials such as explosives, chemical or biological agents, toxins, nuclear materials, and flammable materials. A gas phase sample can be collected by an injector 210 through the inlet 211. The injector 210 can include an air pump that can draw the gas-phase sample from the ambient environment under the control of the computer processor 170. The gas-phase sample collected is pressure fed into the capillary columns 220. The pressure applied to the flowing gas sample and thus the average speed of the gas molecules can be controlled by the computer processor 170. The gas-phase sample can include a mixture of chemicals each having different molecular properties. The capillary columns 220 can produce different amounts of frictions on the flow of the different species of molecules such that they can be separated through the length of the capillary columns 220 to produce phase separated gas 251. For example, lighter weight gas molecules tend to move faster than heavier molecules. The absorption to the side walls of the capillary columns 220 can also affect the mobility of the gas molecules. The fast moving gas phase molecules can exit the capillary columns 220 and enter the gas chamber 240 first, followed by the slow moving molecules. The molecules in the phase separated gas 251 can be adsorbed to the micro-structured surfaces on the Raman sensor substrate 140. The Raman spectrometer unit 150 can measure the Raman spectrum of the adsorbed molecules at the micro-structured surfaces on the Raman sensor substrate 140. The Raman spectra are measured at different times as different molecules enter the gas chamber 240 and become adsorbed by the micro-structured surfaces on the Raman sensor substrate 140.

In one implementation, a same Raman sensor substrate 140 can be used to adsorb different molecules from the gas phase. The late coming molecules can at least partially replace some of the earlier adsorbed molecules on the micro-structured surfaces on the Raman sensor substrate 140. Alternatively, Raman sensor substrate 140 can be replaced over time to provide fresh micro-structured surfaces to adsorb molecules as new species of molecules enter the gas chamber 240.

In one implementation, the temperature of the capillary columns 220 can be control led by the temperature controller 260 to enhance the separation of the molecules. For example, the temperature of the capillary columns 220 can be controlled at a relatively high temperature at the initial stage of the gas-phase separation to accelerate the movement of the fast moving gas molecules. The temperature of the capillary columns 220 can be decreased over time to slow down the slow moving gas-phase molecules. The temperature gradient can thus lengthen the time separation between the fast moving and slow moving molecules, which can increase collection time for the spectral data, and thus increase signal-to-noise ratio in the Raman spectra.

Figure 3:
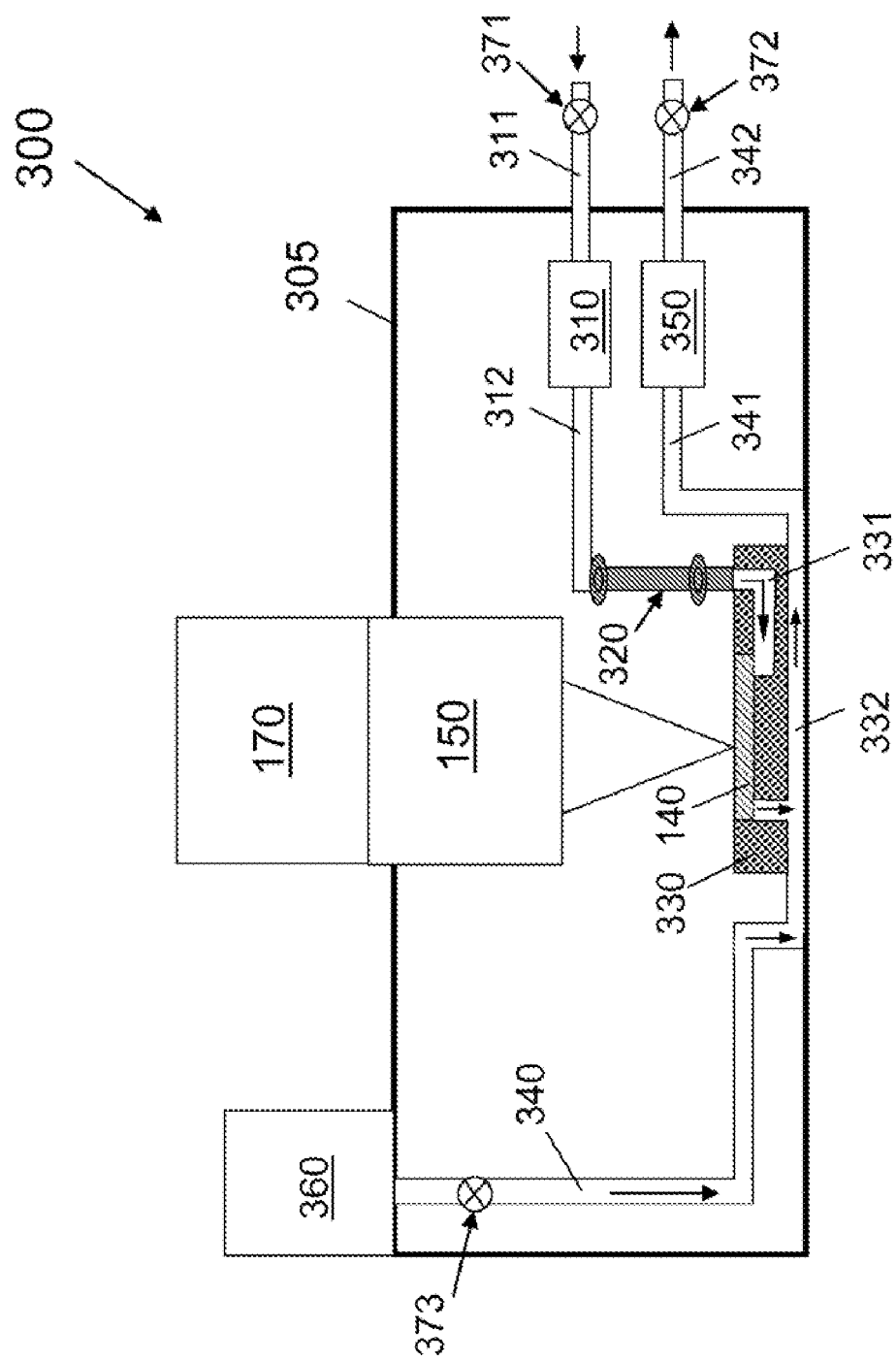
FIG. 3 is a schematic diagram of an exemplified integrated Raman scattering liquid chemical separation device.

In another exemplified implementation, referring to FIG. 3, an integrated Raman scattering liquid chemical separation device 300 can include a device body 305, an inlet 311 mounted on the device body 305, a fluidic pump 310, a separation LC column 320 in fluid connection with the fluidic pump 310 via a feed line 312, a substrate 330 having fluid conduits 331-332, a fluidic pump 350 in fluidic connection with the fluid conduit 332 via the return line 341, and an outlet 342 mounted on the device body 305 and in fluidic communication with the fluidic pump 350. The fluid conduits 331-332 are connected with a Raman sensor substrate 140 and can bring a fluid to the vicinity of the microscopic surfaces of the Raman sensor substrate 140. The device body 305 is a rigid enclosure that can contain, hold, or be mounted with the various components described above. For example, the device body can be a chassis, a cabinet, or a chamber that is made of one or more rigid materials.

The Raman scattering liquid chemical separation device 300 can also include a solvent reservoir 360 that can provide solvent through feed line 340 to the fluid conduit 332, and one or more valves 371-373 for opening or closing the fluid flow through the conduits and the pumps. The Raman scattering liquid chemical separation device 300 can also include a Raman spectrometer unit 150 and a computer processor 170. The computer processor 170 can control the fluidic pumps 310 and 350, and optionally the valves 371-373. The substrate 300 can be mounted at the bottom of the device body 305. The feed line 340, the inlet 311, the outlet 342, and the Raman spectrometer unit 150 can be mounted on the device body 305. The integrated Raman scattering liquid chemical separation device 300 can be configured as a compact single piece of equipment that can easily be transported to a deployment location.

In operation, valves 371-373 are opened. A liquid containing a mixture of chemicals can be pumped by the fluidic pump 310 to the separation LC column 320 via the feed line 312. The separation LC column 320 can separate the chemical compounds to cause the different types of molecules to flow out of the separation LC column 320 at different times into the fluid conduit 331. The fluid carrying separated molecules are transported to the microscopic surfaces of the Raman sensor substrate 140, wherein the molecules can adsorb to the microscopic surfaces. As described above, the Raman sensor substrate 140 can include structures such as holes or rods in diameters in the range from a nanometer to a few hundred nanometers. The surfaces of the structures can be coated with material that has high affinity to the molecules to be detected. The effluent fluid exits the Raman sensor substrate 140 and flows into the conduit 332 and the return line 341, and is finally pumped out of outlet 342 by the fluidic pump 350. The solvent reservoir 360 can provide solvent to the conduit 332 and the return line 341 to balance the flow rate and pressure distribution produced by the pumps 310 and 350.

In some embodiments, the Raman scattering gas chemical separation device 200 or the Raman scattering liquid chemical separation device 300 can include a sensor controller 160 (FIG. 1) that can a temperature bias, an electric field, or a magnetic field to the Raman sensor substrate 140. For example, the sensor controller 160 can apply cooling to the Raman sensor substrate 140 can enhance the adsorption of molecules to the microscopic surfaces and thus enhance the Raman spectral signals. The cooling is especially important considering the heating created at the micro structures by the laser beam emitted by the laser source 410. The sensor controller 160 can be controlled by the computer processor 170. The integrated Raman scattering liquid chemical separation device can be made compact. For example, the device body 305 of the integrated Raman scattering liquid chemical separation device can have compact dimensions of 6"×8"×6" (Width×Length×Height).

Embodiments may include one or more of the following advantages. The disclosed system and methods provide an integrated device that can perform chemical separation and Raman scattering to detect and analyze trace amount of chemicals. The disclosed integrated device can significantly enhance detection sensitivity by using replaceable Raman sensor substrate having nanometer-scale structures and associated surfaces that can adsorb the molecules of the chemical to be detected. The detection sensitivity can also be increased by optimizing the directions of the polarized incident laser beam and the scattered laser light relative to the orientations of the nanometer-scale structures in the Raman sensor substrate.

The disclosed system and methods also provide a compact and integrated chemical separation and Raman scattering device with reduced number of components, decreased footprint, and thus reduced system costs. The integrated chemical separation and Raman scattering device can be easily transported and deployed at locations convenient for sample collection, which allows fast measurement turn around.

The disclosed systems and methods can also be flexibly applied to a variety of chemical separation technologies such as high performance liquid chromatography (HPLC), gas chromatography (GC), and ion chromatography, etc. In another example, the disclosed system and methods is compatible with chemical separation using molecular sieves. Molecular sieves typical have molecular structures that can trap analyte chemicals to allow unwanted other chemicals to be separated. For example, a molecular sieve material is Zeolite that includes holes for trapping target chemicals from a gas or a liquid. Specifically, nano particles made of polymers, metal beads, chemical beads, and other synthetic compounds can be arranged to be at the surfaces of the sieve holes. The nano particles can be engineered to enhance the trapping of the analyte chemicals and enhance Raman scattering signals. The molecular sieves can be used to separate chemicals from a liquid or a gas in the disclosed integrated Raman scattering liquid chemical separation device or integrated Raman scattering gas chemical separation device.

It is understood that the disclosed system and methods are compatible with different types of chemical separation techniques in addition to HPLC, LC, GC, and IC. The disclosed system and methods are compatible with different types of chemical separation techniques. The computer processor can include wired or wireless communication devices to allow the Raman scattering fluid chemical separation devices to communicate with remote computers or to be controlled by remote computers. Chemicals can thus be monitored and detected by remote Raman scattering fluid chemical separation devices and measurement results fed to a home computer in real time. The optical system can exist in different arrangements to facilitate the laser illumination and scattered light collection.

Although specific embodiments of the present invention have been illustrated in the accompanying drawings and described in the foregoing detailed description, it will be understood that the invention is not limited to the particular embodiments described herein, but is capable of numerous rearrangements, modifications, and substitutions without departing from the scope of the invention. For example, the disclosed system is compatible with different computer devices that can access the website, and different layouts and different forms of web user interfaces on computer devices.

What is claimed is:

1. An integrated chemical separation device, comprising:
   a single device body;
   a chemical separation unit configured to separate a chemical from a fluid;
   a Raman sensor substrate comprising a plurality of nano rods on the Raman sensor substrate or nano holes in the Raman sensor substrate, wherein the plurality of nano rods or nano holes comprise surfaces configured to be adsorbed by molecules of the chemical from the fluid; and
   a Raman scattering spectrometer unit configured to emit a laser beam to illuminate the molecules adsorbed on the surfaces of the plurality of nano rods or nano holes in the Raman sensor substrate and to detect the chemical from the light scattered from the molecules adsorbed on the surfaces of the plurality of nano rods or nano holes in the Raman sensor substrate, wherein the chemical separation unit, the Raman sensor substrate, and the Raman scattering spectrometer unit are held in or mounted to the single device body.

2. The integrated chemical separation device of claim 1, wherein the plurality of nano rods having diameters in the range from 1 nanometer to 1000 nanometers.

3. The integrated chemical separation device of claim 1, wherein the plurality of nano holes having diameters in the range from 1 nanometer to 1000 nanometers.

4. The integrated chemical separation device of claim 1, wherein the chemical separation unit is configured to separate the chemical from a gas.

5. The integrated chemical separation device of claim 4, wherein the chemical separation unit comprises one a capillary column or a molecular sieve, each of which being configured to separate the chemical from the gas.

6. The integrated chemical separation device of claim 5, further comprising an injector configured to inject the gas into the capillary column.

7. The integrated chemical separation device of claim 1, wherein the chemical separation unit is configured to separate the chemical from a liquid.

8. The integrated chemical separation device of claim 7, wherein the chemical separation unit comprises a separation liquid chromatography (LC) column or a molecular sieve, each of which being configured to separate the chemical from the liquid.

9. The integrated chemical separation device of claim 7, further comprising a first pump configured to pump the liquid through the chemical separation unit and to the Raman sensor substrate.

10. The integrated chemical separation device of claim 9, further comprising:
    a second pump configured to pump an effluent liquid away from the Raman sensor substrate and out of the integrated chemical separation device; and
    a solvent reservoir configured to provide a solvent to merge with the effluent liquid to be pumped out of the integrated chemical separation device.

11. The integrated chemical separation device of claim 1, further comprising one or more valves configured to control a flow of the fluid to the surfaces of the nano rods or nano holes.

12. The integrated chemical separation device of claim 1, wherein the Raman sensor substrate comprises a fluid conduit configured to transport a liquid to the vicinity of the surfaces of the plurality of nano rods or nano holes to allow the molecules of the chemical to adsorb to the surfaces of the nano rods or nano holes.

13. The integrated chemical separation device of claim 1, further comprising a sensor controller configured to produce a temperature bias, an electric field, or a magnetic field to the Raman sensor substrate to assist adsorption of molecules of the chemical from the fluid on the surfaces of the nano rods or nano holes.

14. The integrated chemical separation device of claim 1, further comprising a chemical separation controller configured to control the chemical separation unit to separate of the chemical from the fluid.

15. The integrated chemical separation device of claim 14, wherein the chemical separation controller is configured to control temperature or a pressure of the fluid in the chemical separation unit to assist the separation of the chemical from the fluid.

16. The integrated chemical separation device of claim 1, wherein the Raman scattering spectrometer unit comprises:
    a laser source configured to emit the laser beam to illuminate the molecules adsorbed on the surfaces of the plurality of nano rods or nano holes in the Raman sensor substrate; and
    a Raman spectrometer configured to produce a Raman spectrum in response to scattered light from the molecules adsorbed on the surfaces of the plurality of nano rods or nano holes in the Raman sensor substrate.

17. The integrated chemical separation device of claim 16, further comprising a computer processor configured to detect the chemical using the Raman spectrum.

18. The integrated chemical separation device of claim 17, wherein the computer processor is held in or onto the single device body.

19. The integrated chemical separation device of claim 1, further comprising:
    a sensor controller configured to control the temperature or to apply an electric field or an magnetic field to the Raman sensor substrate to assist adsorption of molecules of the chemical from the fluid on the surfaces of the nano rods or nano holes;

a chemical separation controller configured to control temperature or pressure of the fluid in the chemical separation unit; and a computer processor configured to control the sensor controller, or the chemical separation controller, or both the sensor controller and the chemical separation controller, wherein the sensor controller, the chemical separation controller, and the computer processor are held in or mounted to the single device body.

20. An integrated chemical separation device, comprising:
a single device body;
a chemical separation unit configured to separate a chemical from a fluid;
a Raman sensor substrate comprising a plurality of nano rods or nano holes having diameters in the range from 0.5 nanometers to 1000 nanometers, wherein the plurality of nano rods or nano holes comprise surfaces configured to be adsorbed by molecules of the chemical from the fluid;
a fluid conduit configured to transport the fluid to the vicinity of the surfaces to allow the molecules of the chemical to adsorb to the surfaces of the nano rods or nano holes; and
a Raman scattering spectrometer unit comprising:
a laser source configured to emit the laser beam to illuminate the molecules adsorbed on the surfaces of the plurality of nano rods or nano holes in the Raman sensor substrate; and
a Raman spectrometer configured to produce a Raman spectrum for detecting the chemical in response to scattered light from the molecules adsorbed on the surfaces of the plurality of nano rods or nano holes in the Raman sensor substrate, wherein the chemical separation unit, the Raman sensor substrate, and the Raman scattering spectrometer unit are held in or mounted to the single device body.

21. The integrated chemical separation device of claim 20, further comprising a sensor controller configured to produce a temperature bias, an electric field, or a magnetic field to the Raman sensor substrate to assist adsorption of the chemical to the surfaces of the nano rods or nano holes.

22. The integrated chemical separation device of claim 20, further comprising a chemical separation controller configured to control temperature or a pressure of the liquid in the chemical separation unit to separate of the chemical from the fluid.

23. The integrated chemical separation device of claim 20, further comprising:
a sensor controller configured to control the temperature or to apply an electric field or an magnetic field to the Raman sensor substrate to assist adsorption of the chemical to the surfaces;
a chemical separation controller configured to control temperature or pressure of the fluid in the chemical separation unit; and
a computer processor configured to control the sensor controller, or the chemical separation controller, or a combination thereof, wherein the sensor controller, the chemical separation controller, and the computer processor are held in or mounted to the single device body.

24. The integrated chemical separation device of claim 20, wherein the plurality of nano rods or nano holes in the Raman sensor substrate have center-to-center spacing in the range from 0.5 nanometers to 1000 nanometers.

25. The integrated chemical separation device of claim 20, wherein the plurality of nano rods have heights in the range from 0.5 nanometers to 1000 nanometers.

26. The integrated chemical separation device of claim 20, wherein the plurality of nano holes have depths in the range from 0.5 nanometers to 1000 nanometers.

27. An integrated chemical separation device, comprising:
a single device body;
a chemical separation unit comprising:
one or more capillary columns configured to separate the chemical from a gas; and
an injector configured to inject the gas into the one or more capillary columns;
a Raman sensor substrate comprising a plurality of nano rods on the Raman sensor substrate or nano holes in the Raman sensor substrate, wherein the plurality of nano rods or nano holes comprise surfaces configured to be adsorbed by molecules of the chemical from the gas;
a fluid conduit configured to transport the gas to the vicinity of the surfaces to allow the molecules of the chemical to adsorb to the surfaces of the nano rods or nano holes; and
a Raman scattering spectrometer unit comprising:
a laser source configured to emit the laser beam to illuminate the molecules adsorbed on the surfaces of the plurality of nano rods or nano holes in the Raman sensor substrate; and
a Raman spectrometer configured to produce a Raman spectrum for detecting the chemical in response to scattered light from the molecules adsorbed on the surfaces of the plurality of nano rods or nano holes in the Raman sensor substrate, wherein the chemical separation unit, the Raman sensor substrate, and the Raman scattering spectrometer unit are held in or mounted to the single device body.

28. The integrated chemical separation device of claim 27 further comprising a sensor controller configured to apply a temperature bias, an electric field, or a magnetic field to the Raman sensor substrate to assist adsorption of the chemical to the surfaces of the nano rods or nano holes.

29. The integrated chemical separation device of claim 27, further comprising a chemical separation controller configured to control temperature or a pressure of the liquid in the chemical separation unit to separate of the chemical from the gas.

30. The integrated chemical separation device of claim 27, further comprising:
a sensor controller configured to control the temperature or to apply an electric field or an magnetic field to the Raman sensor substrate to assist adsorption of the chemical to the surfaces;
a chemical separation controller configured to control temperature or pressure of the gas in the chemical separation unit; and
a computer processor configured to control the sensor controller, or the chemical separation controller, or both the sensor controller and the chemical separation controller, wherein the sensor controller, the chemical separation controller, and the computer processor are held in or mounted to the single device body.

31. The integrated chemical separation device of claim 27, wherein the Raman sensor substrate comprises a plurality of nano rods or nano holes having diameters in the range from 0.5 nanometers to 1000 nanometers, wherein the plurality of nano rods or nano holes comprise surfaces configured to be adsorbed by molecules of the chemical from the gas.

32. The integrated chemical separation device of claim 31, wherein the plurality of nano rods or nano holes in the Raman sensor substrate have center-to-center spacing in the range from 0.5 nanometers to 1000 nanometers.

33. The integrated chemical separation device of claim 31, wherein the plurality of nano rods have heights in the range from 0.5 nanometers to 1000 nanometers.

34. The integrated chemical separation device of claim 31, wherein the plurality of nano holes have depths in the range from 0.5 nanometers to 1000 nanometers.

35. An integrated chemical separation device, comprising:
a single device body;
a separation liquid chromatography (LC) column configured to separate the chemical from a liquid;
a first pump configured to pump the liquid through the separation LC column and to the Raman sensor substrate;
a Raman sensor substrate comprising a plurality of nano rods on the Raman sensor substrate or nano holes in the Raman sensor substrate, wherein the plurality of nano rods or nano holes comprise surfaces configured to be adsorbed by molecules of the chemical from the liquid;
a fluid conduit configured to transport the liquid to the vicinity of the surfaces to allow the molecules of the chemical to adsorb to the surfaces of the nano rods or nano holes; and
a Raman scattering spectrometer unit comprising:
a laser source configured to emit the laser beam to illuminate the molecules adsorbed on the surfaces of the plurality of nano rods or nano holes in the Raman sensor substrate; and
a Raman spectrometer configured to produce a Raman spectrum for detecting the chemical in response to scattered light from the molecules adsorbed on the surfaces of the plurality of nano rods or nano holes in the Raman sensor substrate, wherein the chemical separation unit, Raman sensor substrate, and Raman scattering spectrometer unit are held in or mounted to the single device body.

36. The integrated chemical separation device of claim 35, further comprising:
a second pump configured to pump an effluent liquid away from the Raman sensor substrate and out of the integrated chromatography device; and
a solvent reservoir configured to provide a solvent to merge with the effluent liquid to be pumped out of the integrated chromatography device.

37. The integrated chemical separation device of claim 35, further comprising a sensor controller configured to apply a temperature bias, an electric field, or a magnetic field to the Raman sensor substrate to assist adsorption of the chemical to the surfaces of the nano rods or nano holes.

38. The integrated chemical separation device of claim 35, further comprising a chemical separation controller configured to control temperature or a pressure of the liquid in the chemical separation unit to separate of the chemical from the plurality of chemicals in the liquid.

39. The integrated chemical separation device of claim 35, further comprising:
a sensor controller configured to control the temperature or to apply an electric field or an magnetic field to the Raman sensor substrate to assist adsorption of the chemical to the surfaces of the nano rods or nano holes;
a chemical separation controller configured to control temperature or pressure of the liquid in the chemical separation unit; and
a computer processor configured to control the sensor controller, or the chemical separation controller, or both the sensor controller and the chemical separation controller, wherein the sensor controller, the chemical separation controller, and the computer processor are held in or mounted to the single device body.

40. The integrated chemical separation device of claim 35, wherein the Raman sensor substrate comprises a plurality of nano rods or nano holes having diameters in the range from 0.5 nanometers to 1000 nanometers, wherein the plurality of nano rods or nano holes comprise surfaces configured to be adsorbed by molecules of the chemical from the liquid.

41. The integrated chemical separation device of claim 40, wherein the plurality of nano rods or nano holes in the Raman sensor substrate have center-to-center spacing in the range from 0.5 nanometers to 1000 nanometers.

42. The integrated chemical separation device of claim 40, wherein the plurality of nano rods have heights in the range from 0.5 nanometers to 1000 nanometers.

43. The integrated chemical separation device of claim 40, wherein the plurality of nano holes have depths in the range from 0.5 nanometers to 1000 nanometers.

* * * * *